United States Patent
Frericks et al.

(10) Patent No.: US 6,901,297 B2
(45) Date of Patent: May 31, 2005

(54) STIMULATION ELECTRODE AND ITS USE

(75) Inventors: Matthias Frericks, Hanau (DE); Frank Krüger, Bruchköbel (DE); Heiko Specht, Aschaffenburg (DE)

(73) Assignee: W.C. Heraeus GmbH & Co. KG, Hanau (DE)

( * ) Notice: Subject to any disclaimer, the term of this patent is extended or adjusted under 35 U.S.C. 154(b) by 0 days.

(21) Appl. No.: 10/718,228

(22) Filed: Nov. 19, 2003

(65) Prior Publication Data

US 2004/0133258 A1 Jul. 8, 2004

(30) Foreign Application Priority Data

Nov. 20, 2002 (DE) .......................................... 102 54 287

(51) Int. Cl.$^7$ ................................................. A61N 1/05
(52) U.S. Cl. ...................... 607/121; 607/119; 607/116; 600/374
(58) Field of Search ................................ 607/122, 127, 607/119, 116, 126, 128–131, 121; 600/373–377

(56) References Cited

U.S. PATENT DOCUMENTS

| | | | | |
|---|---|---|---|---|
| 4,566,467 A | * | 1/1986 | DeHaan | 607/116 |
| 4,602,637 A | | 7/1986 | Elmqvist et al. | |
| 4,603,704 A | * | 8/1986 | Mund et al. | 607/116 |
| 4,679,572 A | * | 7/1987 | Baker, Jr. | 607/127 |
| 4,784,160 A | * | 11/1988 | Szilagyi | 607/116 |
| 5,683,443 A | * | 11/1997 | Munshi et al. | 607/121 |
| 6,430,447 B1 | * | 8/2002 | Chitre et al. | 607/121 |
| 2001/0002000 A1 | | 5/2001 | Kumar et al. | |
| 2001/0032005 A1 | | 10/2001 | Gelb et al. | |

FOREIGN PATENT DOCUMENTS

| | | |
|---|---|---|
| DE | 33 00 672 A1 | 7/1984 |
| DE | 42 07 368 A1 | 2/1993 |
| DE | 43 24 185 A1 | 1/1995 |
| DE | 196 45 162 C2 | 8/2001 |
| DE | 196 45 155 C2 | 9/2001 |
| EP | 0 115 778 A1 | 8/1984 |
| EP | 0 116 280 A1 | 8/1984 |
| EP | 0 117 972 A1 | 9/1984 |
| EP | 0 573 275 A2 | 12/1993 |

\* cited by examiner

*Primary Examiner*—Jeffrey R. Jastrzab
(74) *Attorney, Agent, or Firm*—Akin Gump Strauss Hauer & Feld, LLP

(57) ABSTRACT

A stimulation electrode has an electrode surface at least partially covered with a coating of titanium nitride, the titanium nitride having on its side remote from the electrode surface a larger surface than the region of the electrode surface covered by the titanium nitride. The titanium nitride is covered with at least one oxidation protection layer on its surface remote from the electrode surface. The stimulation electrode is useful, for example, in cardiac pacemakers, neuro-stimulation devices and other human implants.

15 Claims, 1 Drawing Sheet

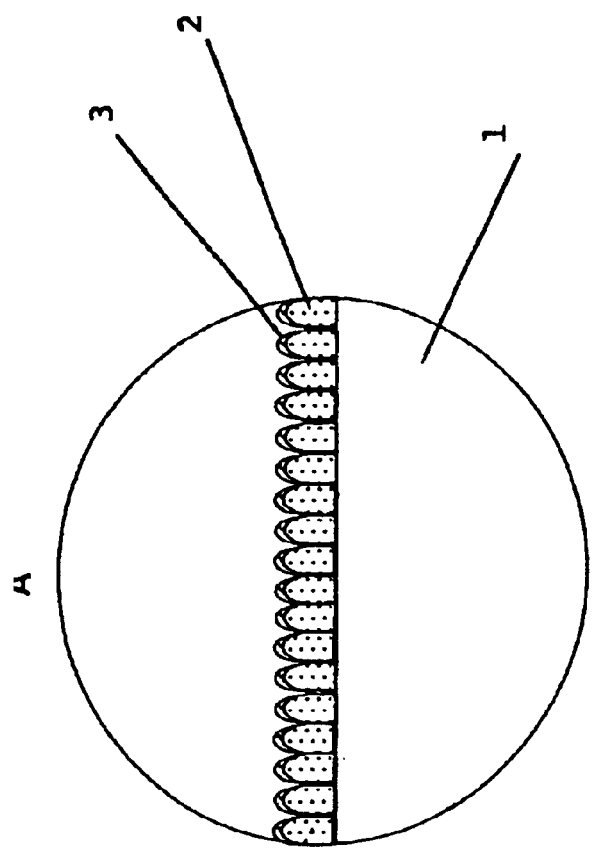
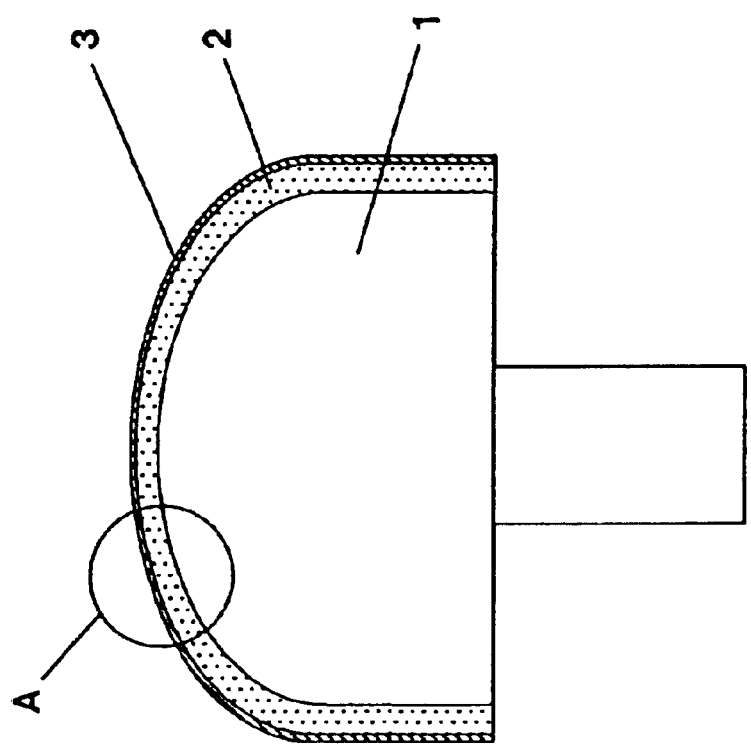
Fig. 1a
Fig. 1

STIMULATION ELECTRODE AND ITS USE

BACKGROUND OF THE INVENTION

The invention relates to a stimulation electrode with an electrode surface which is at least partially covered with a coating of titanium nitride, wherein the titanium nitride has a larger surface on its side remote from the electrode surface than the region of the electrode surface covered with the titanium nitride. The invention further relates to the use of such an electrode.

Such stimulation electrodes are known from German published patent application DE 42 07 368 A1. The stimulation electrode disclosed there is provided with a porous coating, the surface of the porous coating being greater than the surface of the basic surface form of the coated electrode. Nitrides, carbides, carbonitrides or pure metals or alloys of the elements Au, Ag, Ir, Pt and also carbon are disclosed as coating materials. The disclosed stimulation electrode is used as a cardiac pacemaker or neuro-stimulation electrode.

Published U.S. patent application 2001/0002000 A1 discloses substrates of plastic, metals, etc., with a biocompatible coating, which is formed from amorphous titanium nitride. The applications of the substrates are in the field of cardiac pacemakers and electrodes.

European published patent applications EP 117 972 A, EP 116 280 A and EP 115 778 A disclose electrodes for medical applications, provided with porous layers of titanium nitride.

U.S. Pat. No. 4,602,637 discloses a cardiac pacemaker system in which the passive electrode is coated, for example, with activated carbon or titanium nitride.

German published patent application DE 33 00 672 A1 discloses a cardiac pacemaker system with an electrode which has, for example, a coating of titanium nitride.

The publication, J. Riedmüller, A. Bolz, H. Rebling, M. Schaldach, "Improvement of Stimulation and Sensing Performance of Bipolar Pacemaker Leads", Proceedings of the Annual International Conference of the IEEE/EMBS, pp. 2364–2365 (1992), discloses that the use of titanium nitride layers with anodic polarization leads to the formation of oxide layers in the region of the electrode surface. While the physical properties of the titanium nitride are substantially unchanged in stimulation electrodes with a titanium nitride layer which is used as the cathode, this is not the case with use as an anode. The attack by OH— ions leads to the formation of oxide layers, which cause a rise of impedance and therewith also a rise of the threshold voltage. In FIG. 2 of this publication, an iridium-coated titanium electrode is placed opposite one coated with titanium nitride. In anodic operation, the Helmholtz capacity of the titanium nitride-coated electrode falls very much faster than that of the iridium-coated electrode.

BRIEF SUMMARY OF THE INVENTION

The problem is now to provide stimulation electrodes with at least a partial titanium nitride coating, which have a sufficient lifetime in anodic operation.

The problem is solved in that the titanium nitride is covered with at least one oxidation protection layer on its side remote from the electrode surface, wherein at least the side of the oxidation protection layer facing toward the titanium nitride coating is substantially non-porous. By "substantially non-porous" is meant that at least the side of the oxidation protection layer facing the titanium nitride coating should be dense, although it will be understood that during manufacture unavoidable dislocations or pinholes affecting the imperviousness of the layer may occur, at least selectively. The use of an oxidation protection layer on the titanium nitride surface leads to the complete prevention or at least substantial slowing of the formation of oxide layers in the region of the stimulation electrode.

As materials for the stimulation electrode itself, titanium, gold, stainless steel, platinum, platinum-iridium alloys, particularly the alloy Pt90Ir10, and also carbon, are preferred.

It has been found advantageous when the at least one oxidation protection layer reduces the impedance of the stimulation electrode coated with titanium nitride, or else increases the impedance to a maximum value which is smaller than the impedance of the uncoated stimulation electrode.

It has furthermore been found advantageous when the at least one oxidation protection layer has a layer thickness in the range of about 100 nm–5 $\mu$m. Care must be taken that a sufficient oxidation protection action is attained and also that the surface structure of the titanium nitride is not substantially affected. Thus, the layer thickness is, to the extent possible, to be chosen so that the large surface of the titanium nitride is completely or largely retained. In particular, layer thicknesses of the oxidation protection layer in the range of about 100 nm–2 $\mu$m, ideally in a range of about 500 nm to 2 $\mu$m, have been found to be satisfactory.

It is particularly preferred that the oxidation protection layer be biocompatible. It is preferred that the at least one oxidation protection layer be formed of at least one of the elements iridium, platinum, gold or carbon, but pure platinum or iridium is preferred. It is particularly preferred to form the at least one oxidation protection layer of an oxide, a carbide, a nitride, or a polymer, where of course care must be taken that materials are used which reduce the impedance of the stimulation electrode coated with titanium nitride, or else increase the impedance to a maximum value which is smaller than the impedance of the uncoated stimulation electrode.

In particular, it has been found to be satisfactory to use iridium oxide, particularly substoichiometric iridium oxide, as the oxidation protection layer on the titanium nitride.

The at least one oxidation protection layer is preferably formed by a PVD (physical vapor deposition) or CVD (chemical vapor deposition) process. However, formation by spraying, dipping, electrodeposition or a sol-gel process is also possible.

The use of such a stimulation electrode with a titanium nitride layer having an oxidation protection layer arranged thereon as a cardiac pacemaker electrode, neuro-stimulation electrode, or in another human implant is ideal. It is particularly advantageous to use the stimulation electrode as the anode.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown. In the drawings:

FIG. 1 is a side view, partially in section, of a stimulation electrode having a titanium nitride layer and an oxidation protection layer according to one embodiment of the invention;

FIG. 1a is an enlarged diagram of the fragment A from FIG. 1.

DETAILED DESCRIPTION OF THE INVENTION

FIG. 1 shows the stimulation electrode 1. The stimulation electrode may have any shape besides that shown here. Thus, the stimulation electrode 1 can also be embodied in the form of a spiral wire. The electrode surface of the stimulation electrode 1 is partially covered with a coating 2 of titanium nitride. The coating 2 of titanium nitride is here covered on its side remote from the electrode surface of the stimulation electrode 1 with a 1 μm thick oxidation protection layer 3 of iridium.

FIG. 1a shows in detail the fragment A from FIG. 1 in the region of the coatings. It can be seen that the coating 2 of titanium nitride has, on its side remote from the electrode surface of the stimulation electrode 1, a surface which is larger than that of the region of the electrode surface covered with titanium nitride. That is, the surface of the titanium nitride coating 2 is uneven or textured, for example, in this embodiment having hills and valleys. The oxidation protection layer 3 covering the coating 2 of titanium nitride reproduces, to a large extent, the surface structure of the titanium nitride, so that the large surface of the coating 3 of titanium nitride remains completely or largely retained.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A stimulation electrode comprising an electrode surface having at least a partial surface region covered with a coating of titanium nitride, wherein the titanium nitride coating has a larger surface on its side remote from the electrode surface than the region of the electrode surface covered with the titanium nitride, wherein the titanium nitride is covered with at least one oxidation protection layer on its side remote from the electrode surface, and wherein at least a side of the oxidation protection layer facing the titanium nitride is substantially non-porous.

2. The stimulation electrode according to claim 1, wherein the at least one oxidation protection layer reduces an impedance of the stimulation electrode coated with titanium nitride, or alternatively increases the impedance to a maximum value which is smaller than an impedance of the uncoated stimulation electrode.

3. The stimulation electrode according to claim 2, wherein the at least one oxidation protection layer comprises at least one material selected from the group consisting of an oxide, a carbide, a nitride, and a polymer.

4. The stimulation electrode according to claim 3, wherein the at least one oxidation protection layer comprises iridium oxide.

5. The stimulation electrode according to claims 1, wherein the at least one oxidation protection layer has a layer thickness in a range of about 100 nm–5 μm.

6. The stimulation electrode according to claim 5, wherein the layer thickness of the at least one oxidation protection layer is about 100 nm–2 μm.

7. The stimulation electrode according to claim 6, wherein the layer thickness of the at least one oxidation protection layer is about 500 nm–2 μm.

8. The stimulation electrode according to claim 1, wherein the at least one oxidation protection layer is biocompatible.

9. The stimulation electrode according to claim 1, wherein the at least one oxidation protection layer comprises at least one element selected from the group consisting of iridium, platinum, gold, and carbon.

10. The stimulation electrode according to claim 1, wherein the at least one oxidation protection layer is formed by a process selected from the group consisting of a PVD process and a CVD process.

11. The stimulation electrode according to claim 1, wherein the at least one oxidation protection layer is formed by a process selected from the group consisting of spraying, dipping, electrodeposition, and a sol-gel process.

12. The stimulation electrode according to claim 1, in the form of a human implantable electrode.

13. The stimulation electrode according to claim 12, wherein the electrode is a cardiac pacemaker electrode.

14. The stimulation electrode according to claim 12, wherein the electrode is a neuro-stimulation electrode.

15. The stimulation electrode according to claim 12, wherein the stimulation electrode is operated as an anode.

* * * * *